(12) United States Patent
Kim et al.

(10) Patent No.: US 12,305,209 B2
(45) Date of Patent: May 20, 2025

(54) **CROSS-LINKING MATERIAL HAVING ADHESIVE STRENGTH, PREPARED USING *BURKHOLDERIA*-DERIVED TYROSINASE, PREPARATION METHOD THEREFOR, AND APPLICATION THEREOF**

(71) Applicant: SEOUL NATIONAL UNIVERSITY R&DB FOUNDATION, Seoul (KR)

(72) Inventors: Byung Gee Kim, Seoul (KR); Uk Jae Lee, Ulsan (KR); Sang Hyuk Lee, Gunpo-si (KR); Hyun Kim, Pyeongtaek-si (KR)

(*) Notice: Subject to any disclaimer, the term of this patent is extended or adjusted under 35 U.S.C. 154(b) by 1197 days.

(21) Appl. No.: 17/053,748

(22) PCT Filed: May 10, 2019

(86) PCT No.: PCT/KR2019/005607
§ 371 (c)(1),
(2) Date: Nov. 6, 2020

(87) PCT Pub. No.: WO2019/216678
PCT Pub. Date: Nov. 14, 2019

(65) Prior Publication Data
US 2021/0230657 A1    Jul. 29, 2021

(30) Foreign Application Priority Data

May 10, 2018 (KR) .......... 10-2018-0053871
May 3, 2019 (KR) .......... 10-2019-0052248

(51) Int. Cl.
| | |
|---|---|
| *C12P 19/04* | (2006.01) |
| *A61L 24/00* | (2006.01) |
| *A61L 24/10* | (2006.01) |
| *B33Y 70/00* | (2020.01) |
| *C12N 9/02* | (2006.01) |
| *C12P 21/02* | (2006.01) |

(52) U.S. Cl.
CPC .......... *C12P 19/04* (2013.01); *A61L 24/0026* (2013.01); *A61L 24/0031* (2013.01); *A61L 24/104* (2013.01); *C12N 9/0071* (2013.01); *C12P 21/02* (2013.01); *C12Y 114/18001* (2013.01); *A61L 2400/06* (2013.01); *B33Y 70/00* (2014.12)

(58) Field of Classification Search
None
See application file for complete search history.

(56) References Cited

U.S. PATENT DOCUMENTS

2013/0133107 A1    5/2013    Peters et al.

FOREIGN PATENT DOCUMENTS

| KR | 1020100076173 A | 7/2010 | |
|---|---|---|---|
| KR | 1020130011354 A | 1/2013 | |
| KR | 1020160063154 A | 6/2016 | |
| KR | 101799812 B1 | 11/2017 | |
| KR | 20180079233 A | * 7/2018 | ............ C12P 7/22 |

OTHER PUBLICATIONS

Choi et al., Efficient preparation of a permanent chitosan/gelatin hydrogel using an acid-tolerant tyrosinase, Biochemical Eng. J., 129, 2017, 50-56. (Year: 2017).*
Son et al., Structural Basis for Highly Efficient Production of Catechol Derivatives at Acidic pH by Tyrosinase from *Burkholderia thailandensis*, ACS Catal. 8, 2018, 10375-82. (Year: 2018).*
Son et al., Structural Basis for Highly Efficient Production of Catechol Derivatives at Acidic pH by Tyrosinase from *Burkholderia thailandensis*, ACS Catal. 8, Sep. 2018, 10375-82. (Year: 2018).*
Kurisawa et al., Injectable biodegradable hydrogels composed of hyaluronic acid-tyramine conjugates for drug delivery and tissue engineering, Chem. Commn., 2005, 4312-14. (Year: 2005).*
Kim et al. "Enzyme-mediated tissue adhesive hydrogels for meniscus repair" International Journal of Biological Macromolecules 110 (2018) 479-487.
Jin et al. "Enzyme-mediated fast injectable hydrogels based on chitosan-glycolic acid/tyrosine: preparation, characterization, and chondrocyte culture" Polym. Chem. (2014) vol. 5, pp. 391-398.
Partlow et al. "Dityrosine Cross-Linking in Designing Biomaterials" ACS Biomater. Sci. Eng. (2016) vol. 2, pp. 2108-2121.
UniProtKB/Swiss-Prot: Q2T7K1; Tyrosinase (Monophenol monooxygenase); Oct. 31, 2006, 1 page.
KIPO; Office Action dated Oct. 13, 2020 for Application No. 10-2019-0052248.
Jin et al. "Enzymaticaly-crosslinked injectable hydrogels based on biomimetic dextran-hyaluronic acid conjugates for cartilage tissue engineering" Biomaterials, 2010, vol. 31, pp. 3103-3113.
Tan et al. "Injectable in situ forming biodegradable chitosan-hyaluronic acid based hydrogels for cartilage tissue engineering" Biomaterials (2009) vol. 30, pp. 2499-2506.
WIPO; International Search Report and Written Opinion for PCT/KR2019/005607 dated Aug. 19, 2019; 10pp.

* cited by examiner

*Primary Examiner* — Todd M Epstein
(74) *Attorney, Agent, or Firm* — Snell & Wilmer L.L.P.

(57) ABSTRACT

The present invention relates to a cross-linked material having adhesion prepared by using tyrosinase derived from *Burkholderia*, preparation method thereof and application thereof, and specifically relates to the hydrogel composition having adhesiveness. The hydrogel composition having adhesiveness of the present invention is injectable through an injection or spraying, and can be used in 3D printing or preparation of adhesive hydrogel medical film, etc.

3 Claims, 9 Drawing Sheets pH 4 citrate buffer
10w% gelatin
Excess amount of BT_Ty pH 4 Citrate buffer
1w% Chitosan_Tyr
6μM BT_Ty BT_Ty &

CROSS-LINKING MATERIAL HAVING ADHESIVE STRENGTH, PREPARED USING *BURKHOLDERIA*-DERIVED TYROSINASE, PREPARATION METHOD THEREFOR, AND APPLICATION THEREOF

CROSS-REFERENCE TO RELATED APPLICATIONS

This application is the national stage entry of International Application No. PCT/KR2019/005607, filed May 10, 2019, which claims priority to Korean Patent Application No. 10-2018-0053871 filed May 10, 2018 and Korean Patent Application No. 10-2019-0052248 filed May 3, 2019, the disclosures of which are hereby incorporated by reference in their entirety.

TECHNICAL FIELD

The present invention relates to a cross-linked material having adhesion prepared by using tyrosinase derived from *Burkholderia*, preparation method thereof and application thereof.

BACKGROUND ART

For decades in the past, the field of tissue engineering for recovering damaged tissues and functions thereof has been continuously in progress. Among cells, signal substances and scaffolds, which are the three elements of tissue engineering, particularly scaffolds are important elements in leading the successful tissue recovery by providing an optimized environment for the cell growth such as an extracellular matrix (ECM) of the natural tissues. Accordingly, the development of biomimetic scaffolds using the main components of ECM is getting attention.

ECM is mainly consisting of polysaccharides and fibrous proteins, and particularly hyaluronic acid (HA) and collagen account for the most part. The hyaluronic acid is mainly found in ECM of soft connective tissues, and is well-known to have functions such as wound treatment, cellular differentiation and self-recovery of human embryonic stem cell. However, it has restrictions in application to tissue engineering due to non-adhesive properties, and thus it has been a huge task to impart adhesiveness to the hydrogel of hyaluronic acid (HA).

In this regard, crosslinking technology is important in order to form the hydrogel using a biopolymer, because the physical properties of the hydrogel vary depending on how the crosslinking is carried out.

Generally, there are mainly two ways of crosslinking polysaccharides. Firstly, the physical crosslinking is a process by non-covalent bonding such as hydrogen bonding and hydrophobic bonding and does not require an additional agent which may cause toxicity, but has the disadvantages of being sensitive to external irritation such as heat, pH and pressure. In contrast, the chemical crosslinking is a process by C—C, C—X, X-X (wherein C is carbon and X is oxygen, nitrogen, or sulfur) covalent bonding between polymer chains, and thus it can make a structure with high strength. However, photoinitiators necessary for radical polymerization or crosslinking agents such as formaldehyde and glutaraldehyde necessary for condensation may cause damage to the cells, and the form can be made only in vitro, and thus the use is impossible for minimal invasion. Accordingly, enzyme crosslinking agents for forming a stereostructure by covalent bonding are getting attention recently, and it has advantages that there are no side reactions by the substrate specificity of the enzyme and the reaction conditions are suitable for the living body.

The enzymes used for the formation of the hydrogel structure include representatively peroxidase, laccase and tyrosinase. In particular, considerable studies have been in progress for the use of Horseradish peroxidase (HRP) which is one of the peroxidases as the crosslinking agent. This is because there are advantages that gelation is possible in a short time of about 2 to 60 seconds by controlling the concentration of HRP, and hydrogel with relatively high mechanical strength can be made.

However, if the hydrogen peroxide necessary as proton donor exists in a level greater or equal to 0.2 mM, there is a possibility of causing apoptosis, and thus it has a problem that an appropriate amount of hydrogen peroxide within the range that does not cause cell toxicity must be used.

Moreover, an injectable hydrogel crosslinked by using HRP has been reported, but there has been a problem of solidification before the shape is formed because gelation occurs as soon as two separate substances are mixed.

Laccase is also one of the oxidating enzymes and can induce crosslinking between phenol compounds with the only addition of a little amount. However, it takes a long time of about 200 minutes until the gelation is complete, and the hydrogel having a relatively low storage modulus (G') is formed, and thus there is a limit in application to tissue engineering.

Meanwhile, Patent Literature 1 describes the development of an injectable hydrogel using the enzyme reaction with various synthetic, natural, synthetic/natural hybrid polymer as the substrate with phenol or aniline derivatives bonded. Moreover, Patent Literature 2 describes the hydrogel anti-adhesion adjuvant characterized by comprising 0.1 to 10 wt % of tyramine-modified carboxymethylcellulose derivative, 0.5 to 10 wt % of pullulan and 0.1 to 2 wt % of HRP and manufacturing method of the same.

However, in the case of the hydrogel of Patent Literatures 1 and 2, for manufacturing, other than the enzyme, an accelerator is additionally necessary, and they also claim to support the injectable type, and thus they had the disadvantage of failing to have hard physical property to be used in vitro.

Moreover, the Non-Patent Literature 1 shows the hydrogel manufactured through the enzymatic crosslinking reaction by HRP after chemical modification such as coupling tyramine to dextran and hyaluronic acid which are natural biopolymers. The Non-Patent Literature 2 shows the hydrogel manufactured through chemical modification of chitosan and hyaluronic acid which are natural polymers into chitosan bonded to amine group and hyaluronic acid bonded to aldehyde group, respectively, followed by the Schiff's base chemical reaction between the two functional groups.

However, Non-Patent Literatures 1 and 2 have disadvantages that chemical modifications are necessary with respect to both hyaluronic acid and dextran, and chitosan and hyaluronic acid, and the manufactured hydrogel did not have high modulus.

Meanwhile, from the perspective of tissue engineering, hydrogel becomes a scaffold providing the space for the cells to grow. The scaffold or artificial extracellular matrix is used in order to make the cells grow better, or in the desired direction for the purpose of tissue engineering, and thus the hydrogel using biopolymer is being actively used. For such biopolymers, examples such as glycogen, chitosan, cellulose and hyaluronic acid are variously present, and in order to make them into hydrogel, physical or chemical crosslinking process is used.

Accordingly, the hydrogel of hard physical properties can be used in places where physical elements such as patches and films are necessary (surgery, first aid), and the hydrogel of soft physical properties may take the role of storage surrounding low-molecular substance (peptides, antitumor agent, nanoparticles), or cells, and thus in order to be used in the form of patches, fillers and thin films necessary for tissue engineering depending on the physical properties, it is necessary to provide the hydrogel to be effective scaffolds of desired physical properties.

PRIOR ART LITERATURE

Patent Literature (Patent Literature 1) Korean Patent Laid-Open No. 10-2010-0076173
(Patent Literature 2) Korean Patent Laid-Open No. 10-2016-0063154

Non-Patent Literature (Non-Patent Literature 1) Jin R et al., Enzymatically-crosslinked injectable hydrogels based on biomimetic dextran-hyaluronic acid conjugates for cartilage tissue engineering., Biomaterials 31, 2010, 3103-3113
(Non-Patent Literature 2) H. Tan et al., Injectable in situ forming biodegradable chitosan-hyaluronic acid based hydrogels for cartilage tissue engineering., Biomaterials 30, 2009, 2499-2506

DETAILED DESCRIPTION OF THE INVENTION

Technical Subject Matter to be Achieved

The purpose of the present invention is to provide a hydrogel composition which uses various biopolymers such as hyaluronic acid, and has desired physical properties, in particular, adhesiveness, and thereby can be effective scaffold, that is, a cross-linked material having adhesiveness of the degree that is easy for minimal invasion, preparation method thereof and application thereof.

Technical Means for Achieving the Technical Subject Matter

Accordingly, the inventors of the present invention found in order to achieve the task that the hydrogel having adhesiveness can be manufactured where gelation is carried out by crosslinking polymers such as hyaluronic acid with phenol derivative introduced by using tyrosinase derived from *Burkholderia* which imparts adhesiveness to mussel protein as a catalyst. In particular, they found that tyrosinase derived from *Burkholderia thailandensis* has activity even at pH of acidity, and thus where it is used as a catalyst, the hydrogel of acidic pH can be formed. Where hydrogel is formed at acidic pH, the automatic oxidation of DOPA residues formed together with crosslinking of the hydrogel is blocked, and thus considerable content of DOPA can be obtained, and it has characteristics of exhibiting adhesiveness by such DOPA residues.

Specifically, the present invention provides the following.

(1) A method for preparing an adhesive hydrogel composition, the method comprising cross-linking a polymer wherein a phenol derivative is introduced to hyaluronic acid, alginate, chondroitin sulfate, chitosan or polyethylene glycol; gelatin; or albumin; using tyrosinase derived from *Burkholderia*.

(2) The method for preparing an adhesive hydrogel composition according to (1), wherein the composition is prepared from a polymer wherein a phenol derivative is introduced to hyaluronic acid or chitosan.

(3) The method for preparing an adhesive hydrogel composition according to (1), wherein the phenol derivative is tyramine, tyrosine, dopamine, 4-hydroxyphenylacetic acid, 3-(4-hydroxyphenyl) propionic acid or 3,4-dihydroxyphenylacetic acid.

(4) The method for preparing an adhesive hydrogel composition according to (3), wherein the phenol derivative is tyramine.

(5) The method for preparing an adhesive hydrogel composition according to (1), wherein the cross-linking is performed in acidic condition.

(6) The method for preparing an adhesive hydrogel composition according to (5), wherein the acidic condition is in the range from pH 2 to 6.

(7) The method for preparing an adhesive hydrogel composition according to (1), wherein the cross-linking is performed at a temperature in the range from 18 to 45° C., for 5 minutes to 17 hours.

(8) The method for preparing an adhesive hydrogel composition according to (1), wherein the tyrosinase is tyrosinase derived from *Burkholderia thailandensis*.

(9) An adhesive hydrogel composition prepared by the method for preparation of any one of (1) to (8).

(10) The adhesive hydrogel composition according to (9), wherein the composition is injectable through an injection or spraying.

(11) The adhesive hydrogel composition according to (10), wherein the composition is injectable through an injection or spraying to biological tissue.

(12) The adhesive hydrogel composition according to (10), wherein the composition is used in 3D printing.

(13) An adhesive hydrogel film prepared by spraying the adhesive hydrogel composition according to (10).

(14) The adhesive hydrogel film according to (13), wherein the film is a film for prevention of intestinal adhesion or a film for implant coating.

Effects

The present invention relates to a cross-linked material having adhesiveness prepared by using tyrosinase derived from *Burkholderia* as a catalyst, preparation thereof and application thereof, and has the advantage of being capable of producing the hydrogel composition having desired physical properties, in particular, adhesiveness.

Moreover, the present invention relates to the preparation method of the adhesive hydrogel composition injectable through an injection or spraying, and can be used in 3D printing or preparation of adhesive hydrogel medical film, etc.

BRIEF EXPLANATION OF THE DRAWINGS

FIG. 9 shows the storage modulus and loss modulus of gelatin hydrogel crosslinked under the condition of pH 4.0, and FIG. 10 shows the storage modulus and loss modulus of gelatin hydrogel crosslinked under the condition of pH 3.0.

DETAILED CONTENTS FOR CARRYING OUT THE INVENTION

Figure 1:
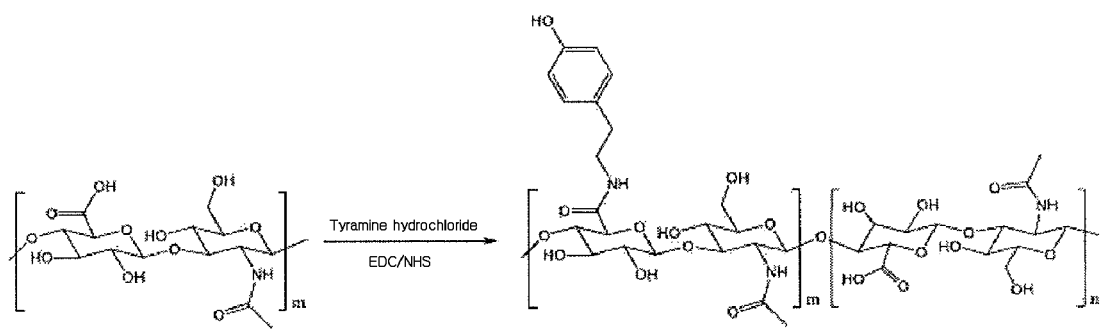
FIG. 1 shows a mimetic diagram of the reaction forming hyaluronic acid-tyramine conjugate by introducing tyramine into hyaluronic acid shown in Experimental Example 2.

Hereinafter, the present invention shall be explained in detail. The present invention can be carried out in various forms and the present invention shall not be construed as being limited to the embodiments described in this text.

Unless defined otherwise, all terms used here, including the technical or scientific terms, mean the same as understood by a skilled person in the art to which the present invention pertains. Generally, the nomenclature used in this specification and the experimental processes described below are well-known in this technical field and are generally used.

The present invention relates to the cross-linked material having adhesiveness prepared by using tyrosinase and preparation method thereof, and the tyrosinase is characterized by being derived from *Burkholderia* (BT_Ty).

That is, the cross-linked material of the present invention is a cross-linked material prepared by using tyrosinase derived from *Burkholderia* as a catalyst in the crosslinking reaction of the polymer compound with a phenol derivative introduced.

Tyrosinase of the present invention converts phenol into catechol by introducing hydroxylation group into an aromatic ring under the presence of oxygen as polyphenol oxidizing enzyme and produces quinone from catechol through an additional oxidizing reaction. Thereafter, because quinone with high reactivity quickly bonds to amine group or thiol group by nucleophile reaction, not only carbon-carbon and carbon-oxygen bonds but also carbon-nitrogen and carbon-sulfur bonds can be formed.

Accordingly, tyrosinase can induce more bonds compared to peroxidase or laccase which form only carbon-carbon and carbon-oxygen bonds and thereby can make gel structure with higher strength. Moreover, because the reaction proceeds under the presence of oxygen without other cofactors, it has the advantage of having milder reaction conditions.

The tyrosinase used as a catalyst of the cross-linking reaction in the present invention is derived from *Burkholderia*, preferably, derived from *Burkholderia thailandensis*.

Meanwhile, for the polymer compounds used in order to prepare the hydrogel of the present invention, polymers wherein a phenol derivative is introduced to hyaluronic acid, alginate, chondroitin sulfate, chitosan or polyethylene glycol (PEG) can be used, and gelatin or albumin can also be used. Preferably, a polymer wherein a phenol derivative is introduced to hyaluronic acid or chitosan can be used.

For the phenol derivative, tyramine, tyrosine, dopamine, 4-hydroxyphenylacetic acid, 3-(4-hydroxyphenyl) propionic acid or 3,4-dihydroxyphenylacetic acid can be used, and preferably tyramine can be used.

In one embodiment of the present invention, the method for preparing the cross-linked material of the present invention comprises the steps below:

(a) preparing a polymer compound wherein a phenol derivative is introduced by introducing a phenol derivative to hyaluronic acid, alginate, chondroitin sulfate, chitosan or polyethylene glycol (PEG), and (b) crosslinking by adding tyrosinase derived from *Burkholderia* as a catalyst to the obtained polymer compound wherein the phenol derivative is introduced.

At this time, the polymer compound wherein the phenol derivative is introduced in the step (a) can be obtained through a process known to a skilled person in the art.

The step (b) is characterized by being carried out in acidic conditions, and the acidic conditions are preferably in the range from pH 2 to 6, more preferably in the range from pH 3 to 4.

Moreover, the step (b) is characterized by being performed at a temperature in the range from 18 to 45° C., preferably at a temperature in the range from 25 to 40° C., and more preferably at a temperature in the range from 30 to 37° C. The reaction can be performed for 5 minutes to 17 hours, but it is preferable for the reaction to be performed for 6 to 8 hours.

In the present invention, tyrosinase derived from *Burkholderia* (BT_Ty) comprises not only purified tyrosinase but also the cell culture medium comprising the microorganism with the tyrosinase expressed, or the cell extract comprising the same. Moreover, the microorganism with the tyrosinase expressed can be used as a whole cell catalyst.

As to the usage of tyrosinase which is a catalyst of the present invention, because tyrosinase can also function as impurities, minimum amount possible should be used in order to maximize the crosslinking efficiency. In this perspective, the preferable amount of tyrosinase used as a catalyst is 3 μM to 600 μM.

In another embodiment of the present invention, an adhesive hydrogel which is injectable through an injection or spraying is prepared. In order to prepare the hydrogel injectable through an injection or spraying, it is necessary to control the mechanical strength and the flexibility of the hydrogel.

The present invention shall be explained in detail through the embodiments below. However, the embodiments are merely for specifying the descriptions of the present invention, and the present invention shall not be limited by the embodiments.

Embodiments

Experimental Example 1: Preparation of Tyrosinase Derived from *Burkholderia thailandensis* (BT_Ty)

The pET28a vector with the gene of tyrosinase derived from *Burkholderia thailandensis* (BT_Ty) inserted was transformed into *E. coli* BL21, followed by spreading it to LB solid medium, and the colony obtained therefrom was inoculated to 3 mL of LB liquid medium containing 50 μg/mL of kanamycin, and was cultured in a shaking incubator at 37° C. for 8 hours. For subculture, kanamycin of 50 μg/mL and 500 μl of seed culture medium are added to 50 mL of LB liquid medium and the cells were cultured in a shaking incubator at 37° C. . . .

When $OD_{600}$ (optical density at 600 nm) reaches to about 0.6, 0.02 mM IPTG or 0.2 mM IPTG and 1 mM $CuSO_4$ were added, and then at 37° C., for 20 hours, protein overexpression was induced. In order to obtain protein, cells were harvested by centrifuging for 10 minutes at 4,000 rpm, and the cells were washed by adding 5 mL of 50 mM tris-hydrochloric acid (Tris-HCl) buffer solution (pH 8.0). Hereto, 5 mL of 50 mM tris-hydrochloric acid buffer solution (pH 8.0) was added again, and cell-lysis was performed by using a ultrasonicator (Vibra & cell, USA). Thereafter, the cell lysate was dispensed to 1.7 mL tube, and was centrifuged for 30 minutes at 16,000 rpm, and the cell extract comprising protein was obtained.

His-tag purification was performed on this cell extract using Ni-NTA column. Firstly by using a pre-binding buffer (5 mM imidazole, 300 mM NaCl, 50 mM Tris-HCl buffer) of 1 column volume, the activity of Ni-NTA was induced, and the cell extract was passed through the Ni-NTA column and tyrosinase was bonded to the column, and then using the wash buffer (25 mM imidazole, 300 mM NaCl, 50 mM Tris-HCl buffer) of twice as much the column volume, the impurities that do not strongly bond to the Ni-NTA column were removed. Lastly, using the elution buffer (250 mM imidazole, 50 mM Tris-HCl), tyrosinase was separated from the Ni-NTA column, and then in order to dilute the imidazole to the level of 1/2500, using 10K filter, the buffer solution was replaced with 50 mM Tris-hydrochloric acid buffer solution, and purified tyrosinase was obtained.

Experimental Example 2: Preparation of Hyaluronic Acid-Tyramine Conjugate

Hyaluronic acid (1.0 g, 2.5 mmol carboxy group) was dissolved in 100 mL (0.01 mol· $L^{-1}$) of distilled water, and to this solution, EDC (ethyl(dimethylaminopropyl) carbodiimide; 1437.75 mg, 7.5 mmol) and NHS (N-hydroxysuccinimide; 863.175 mg, 7.5 mmol), and tyramine hydrochloride (1302.3 mg, 7.5 mmol) were added. Thereafter, the reaction was performed for a night at room temperature, and then the reaction was terminated, and through a dialysis membrane (molecular weight of cutoff MWCO 4,000), while exchanging the distilled water, dialysis was performed for three days. Hyaluronic acid-tyramine (HA-Ty) conjugate which is the final product was obtained as white powder through lyophilization. The tyramine binding rate of HA-Ty conjugate was analyzed with NMR, and in result, tyramine per 100 units of hyaluronic acid was demonstrated to be about 30%.

The mimetic diagram of the reaction forming the hyaluronic acid conjugate was shown in FIG. 1.

Experimental Example 3: Preparation of Hyaluronic Acid Hydrogel Crosslinked by Tyrosinase Derived from *Burkholderia* (BT_Ty)

Figure 4:
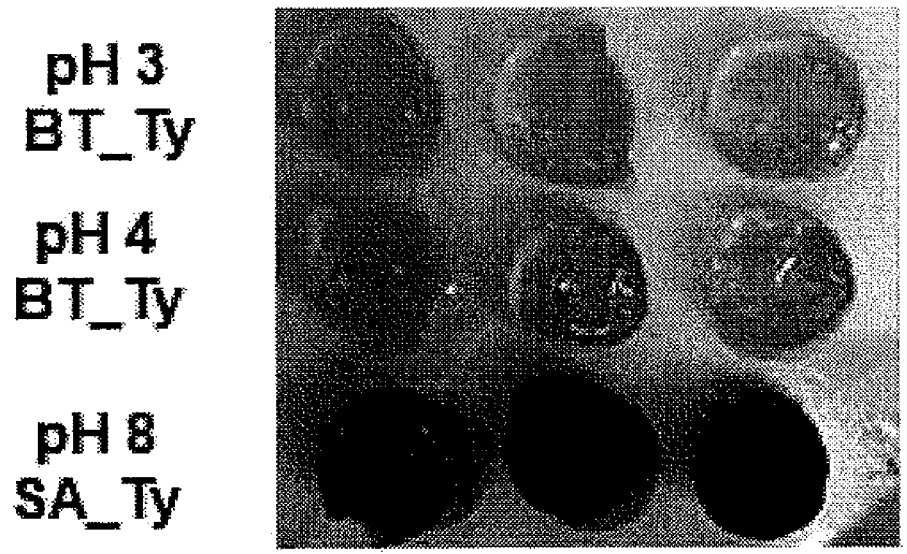
Figure 5:
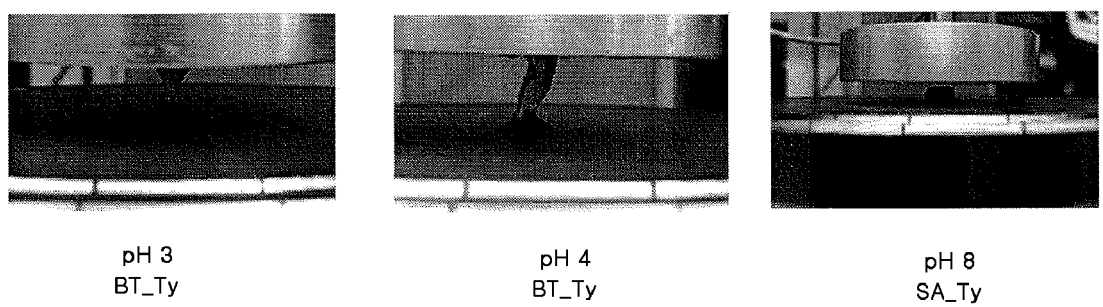
FIG. 5 is a comparison of the adhesiveness of hyaluronic acid hydrogel crosslinked by tyrosinase derived from *Burkholderia* and hyaluronic acid hydrogel crosslinked by *Streptomyces avermitilis* tyrosinase, prepared according to the process of Experimental Example 4.

In order to make hyaluronic acid hydrogel, 2 wt % of HA-Ty conjugate prepared in Experimental Example 2 was dissolved in citric acid buffer solution (pH 3.0 or pH 4.0) or Tris-hydrochloric acid buffer solution (pH 8.0) at 40° C. Thereafter, as a catalyst for crosslinking reaction of HA-Ty conjugate, tyrosinase derived from *Burkholderia* (6 μM) purified according to the process of Experimental Example 1 was added, and then the solution was simply swirled, and was reacted for 8 hours at 37° C. in a PDMS mold of 25 mm in diameter (FIGS. 7 and 8), 8 mm in diameter and 2 mm in thickness (FIGS. 4 and 5).

Figure 2:
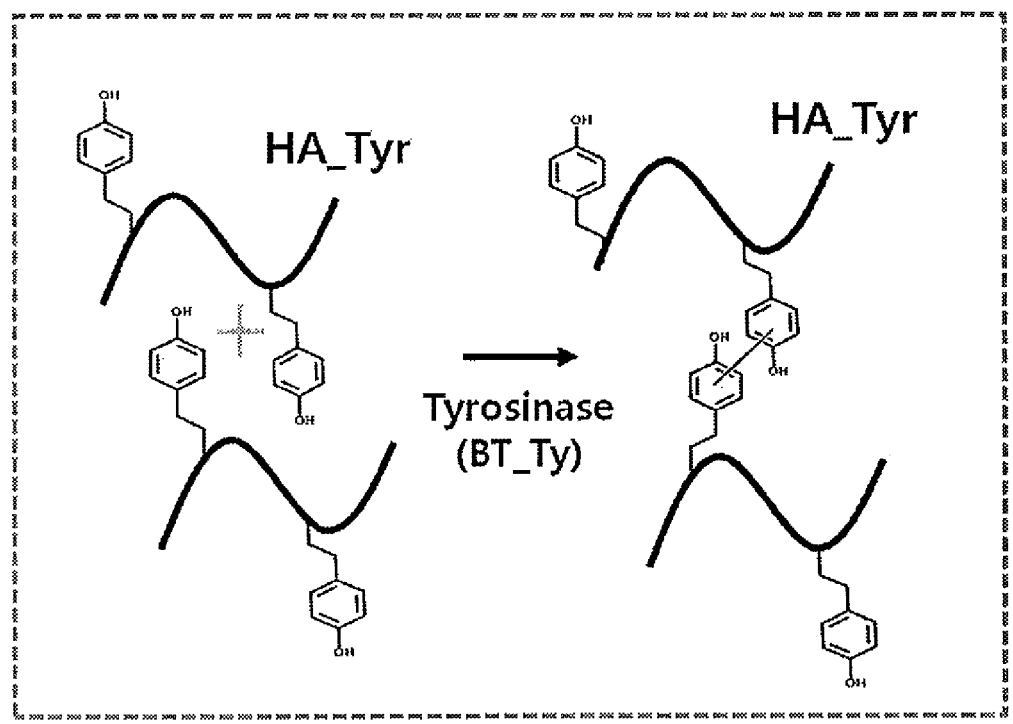
FIG. 2 shows a mimetic diagram of the crosslinking reaction upon the formation of the hyaluronic acid hydrogel shown in Experimental Example 3.

The mimetic diagram of the crosslinking reaction at the time of formation of the hyaluronic acid hydrogel was shown in FIG. 2.

Experimental Example 4: Assessment of Physical Properties of Hyaluronic Acid Hydrogel Crosslinked by Tyrosinase Derived from *Burkholderia* (BT_Ty)

In order to compare physical properties of the hydrogel prepared by using tyrosinase derived from *Burkholderia* of the present invention and the hydrogel prepared by using tyrosinase derived from *Streptomyces avermitilis*, the present experiment was carried out. Firstly, according to the process of Experimental Example 3, hyaluronic hydrogel crosslinked by tyrosinase derived from *Burkholderia* was prepared under various pH conditions (pH 3.0, 4.0 and 8.0). In addition, as comparative examples, a negative control group without tyrosinase added and hyaluronic hydrogel crosslinked by using tyrosinase derived from *Streptomyces avermitilis* as a catalyst instead of tyrosinase derived from *Burkholderia* was prepared through the same experimental process under the same pH conditions as above.

Figure 3:
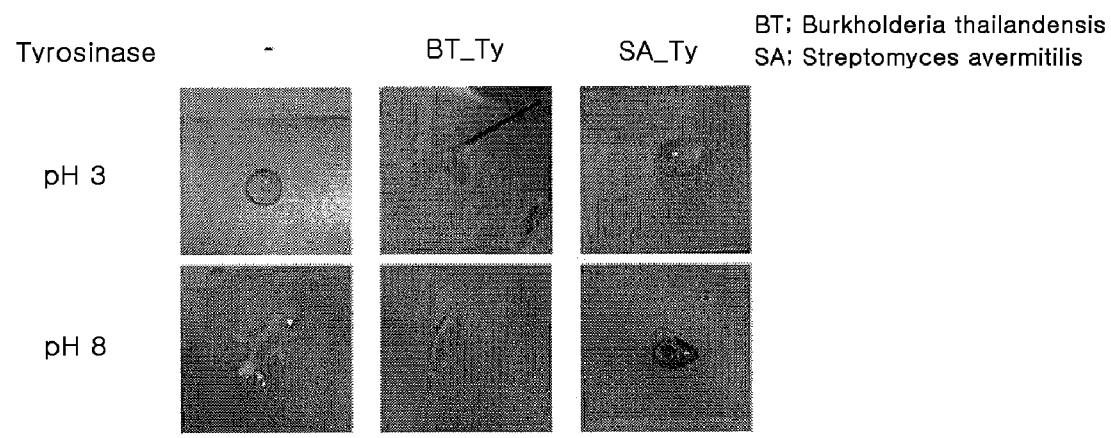
FIG. 3 and FIG. 4 are comparisons of the formation and the colors of hyaluronic acid hydrogel under various pH conditions prepared according to the process of Experimental Example 4.

In result, as shown in FIG. 3, it was verified that in the case of using tyrosinase derived from *Burkholderia* (BT_Ty) as a catalyst, the crosslinking in acidic condition (pH 3.0) has progressed well. In contrast, in the case of using tyrosinase derived from *Streptomyces avermitilis*, it was verified that the crosslinking did not progress in acidic condition (pH 3.0), and the crosslinking progressed only in neutral condition (pH 8.0).

Moreover, in the case of hyaluronic hydrogel crosslinked in acidic condition (pH 3.0) by BT_Ty, compared to the case where tyrosinase was not added, or the case where it is crosslinked in neutral condition (pH 8.0) by SA_Ty, it was verified that its shape change was freer, and it sticks better to the walls.

Meanwhile, comparing the colors of hyaluronic acid hydrogel crosslinked in acidic condition (pH 3.0 or pH 4.0) by BT_Ty and hyaluronic acid hydrogel crosslinked in neutral condition (pH 8.0), as shown in FIG. 4, in the case of hyaluronic acid hydrogel crosslinked in acidic condition (pH 3.0 or pH 4.0) by BT_Ty, it was verified to demonstrate yellow in color. In contrast, in the case of hyaluronic acid hydrogel crosslinked in neutral condition (pH 8.0) by SA_Ty, it demonstrated black in color. The difference in color of the hydrogel seems to result from the difference in substrate specificity of BT_Ty and SA_Ty together with the difference in automatic oxidizing reaction of DOPA residues formed after crosslinking according to pH conditions.

Moreover, in order to compare the adhesiveness of hyaluronic acid hydrogel prepared above, after applying pressure of about 0.1 mN for about 1 minute with universal testing machine (Shimadzu, Japan) to hyaluronic acid hydrogel shown in FIG. 4, the degrees of strength and morphological change were observed while lifting up the hydrogel.

In result, as shown in FIG. 5, it was verified that hyaluronic acid hydrogel crosslinked in acidic condition by BT_Ty in comparison with hyaluronic acid hydrogel crosslinked in neutral condition by SA_Ty sticks better to the compression plate, and stretches better.

Experimental Example 5: Preparation of Gelatin Hydrogel Crosslinked by Tyrosinase Derived from *Burkholderia* (BT_Ty)

10 wt % of gelatin was dissolved in a citric acid buffer solution (pH 4.0), and the product was divided into an experimental group with tyrosinase added and an experimental group without tyrosinase, and then each was reacted for four hours at 37° C.

Figure 6:
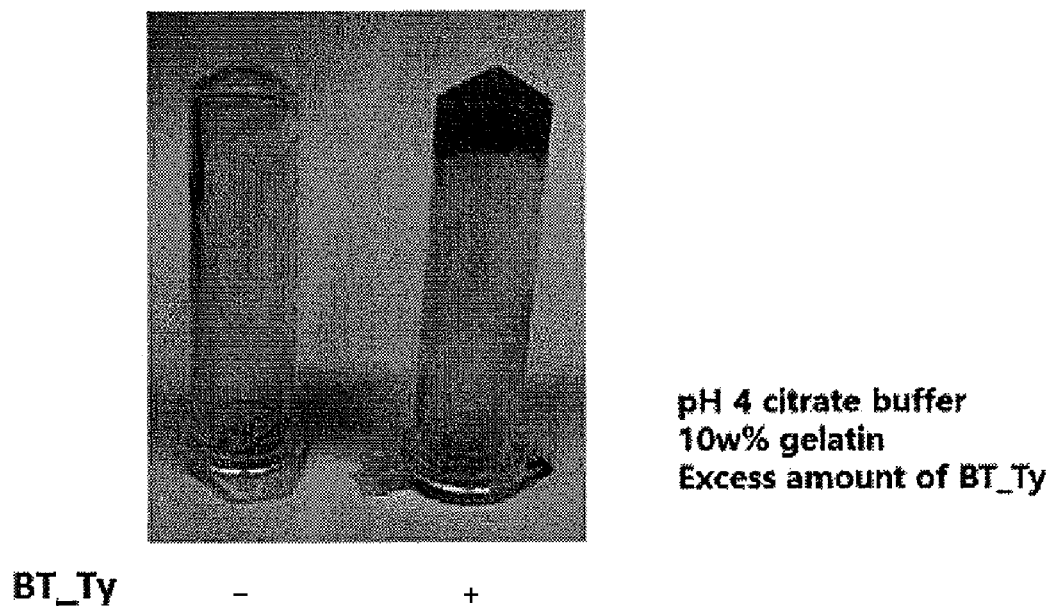
FIG. 6 shows the formation of gelatin hydrogel prepared in Experimental Example 5.

In result, as shown in FIG. 6, in the case of the experimental group without tyrosinase, it existed in liquid state, whereas in the case of the experimental group with tyrosinase added, crosslinking progressed and formation of hydrogel was observed. Cross-linked hydrogel demonstrates brown in color by melanin.

Experimental Example 6: Assessment of Physical Properties of Gelatin Hydrogel Crosslinked by Tyrosinase Derived from *Burkholderia* (BT_Ty)

Figure 7:
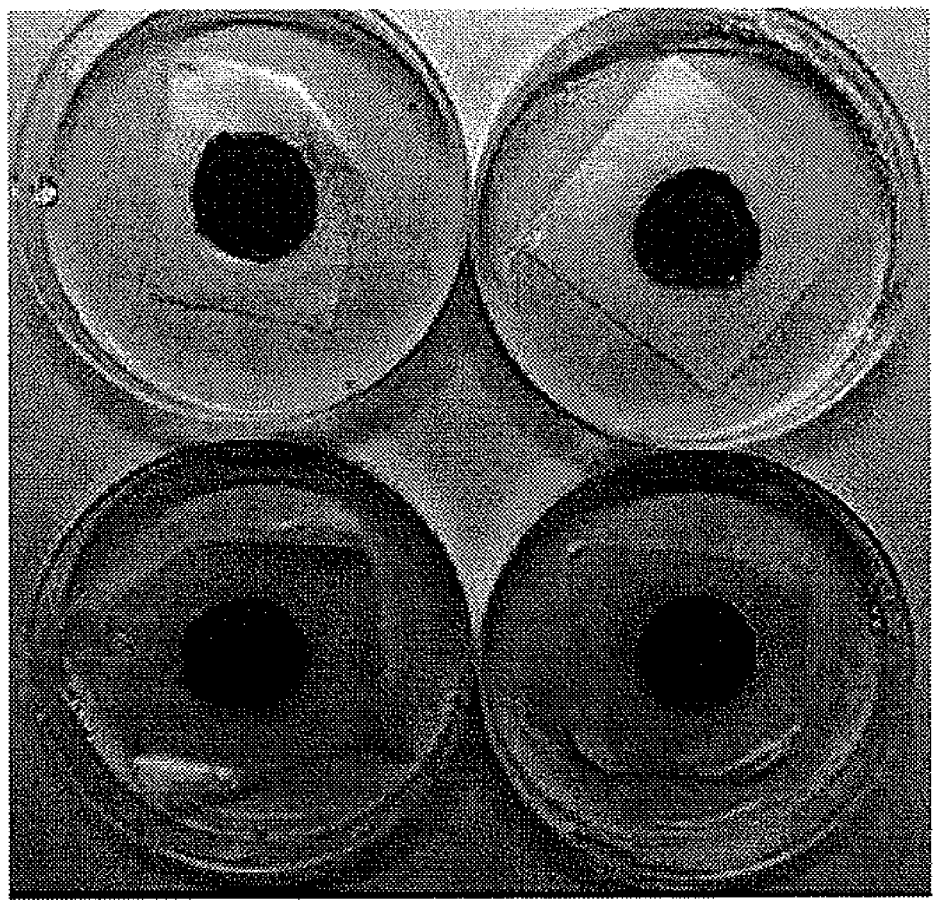
FIG. 7 and FIG. 8 show gelatin hydrogel crosslinked under the condition of pH 4.0 (FIG. 7) and gelatin hydrogel crosslinked under the condition of pH 3.0 (FIG. 8) prepared in Experimental Example 6.
Figure 8:
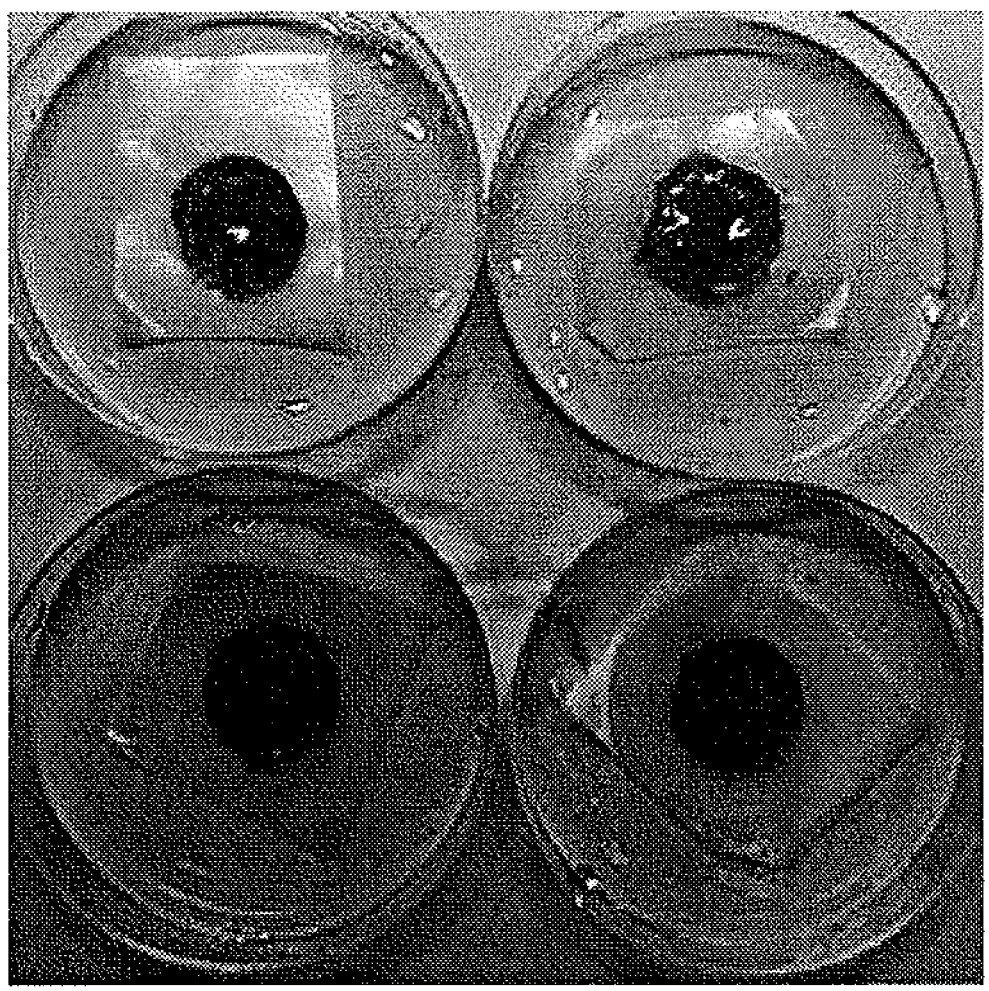
Figure 9:
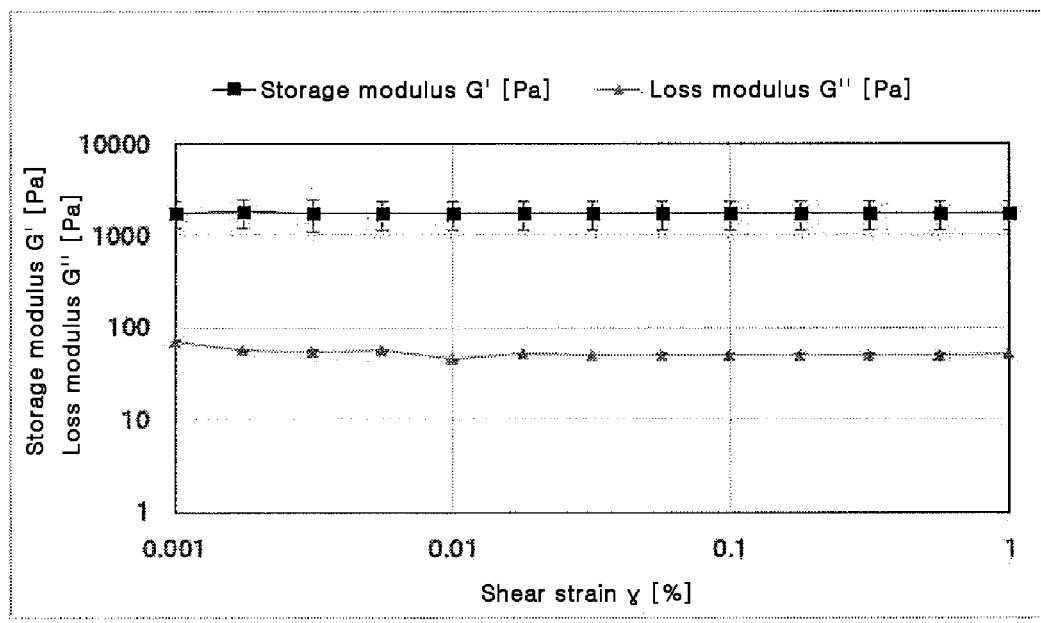
FIG. 9 and FIG. 10 show measurements of the storage modulus and loss modulus of gelatin hydrogel in order to find the rheology of gelatin hydrogel prepared in Experimental Example 6.
Figure 10:
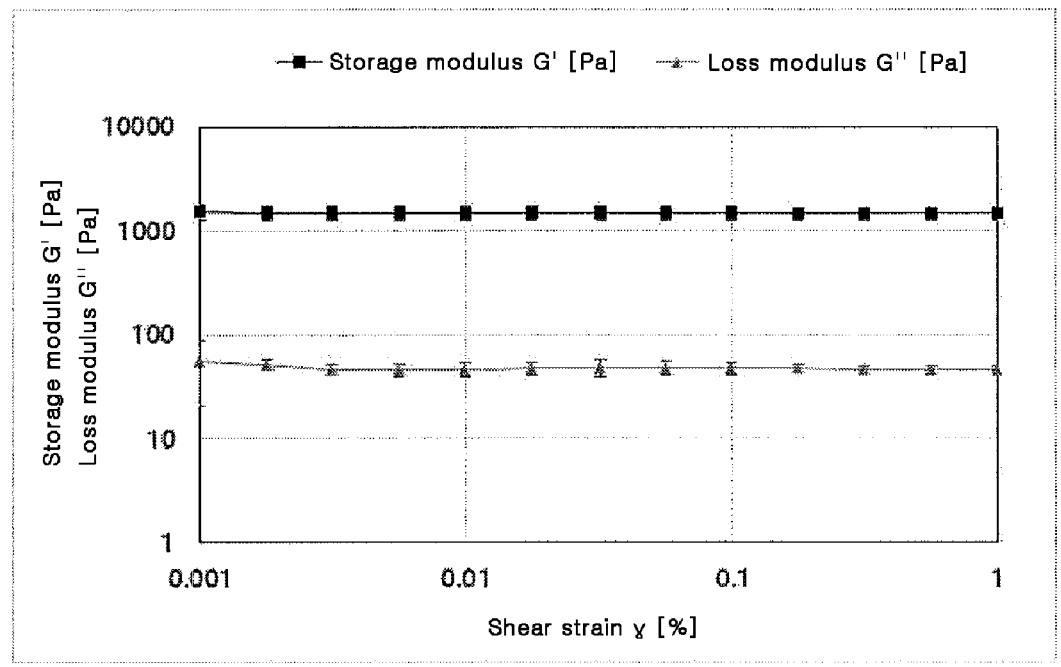

By the same process as Experimental Example 5, cross-linking bonding substance was obtained by crosslinking gelatin under the condition of pH 4.0 (FIG. 7). As a result of independent repetitive experiments carried out four times, identical cross-linked material was obtained. Moreover, cross-linked material was obtained by crosslinking gelatin by having the same conditions as in Experimental Example 5 (FIG. 8), except for changing the pH of citric acid to 3.0. Thereafter, in order to assess physical properties of the two cross-linked material obtained above, the storage modulus and the loss modulus of the two products were each measured (FIGS. 9 and 10).

In result, it was verified that for both cross-linked material, the storage modulus which is a physical property of solid was demonstrated to be high, whereas the loss modulus which is a physical property of liquid was demonstrated to be low. Through the result, it was verified that in both conditions of pH 3.0 and pH 4.0, crosslinking of gelatin by tyrosinase derived from *Burkholderia* was progressed and gelatin hydrogel was formed.

Preparation of Chitosan Hydrogel Crosslinked by Tyrosinase Derived from *Burkholderia* (BT_Ty)

3-(4-hydroxyphenyl) propionic acid was added to chitosan, and then by performing EDC/NHS coupling reaction, chitosan-tyrosine conjugate was prepared. Thereafter, for the final concentration to become 1 wt %, the chitosan-tyrosine conjugate was dissolved in citric acid buffer solution (pH 4.0), and the product was divided into an experimental group without tyrosinase and an experimental group with tyrosinase added, and each was reacted for four hours at 37° C.

Figure 11:
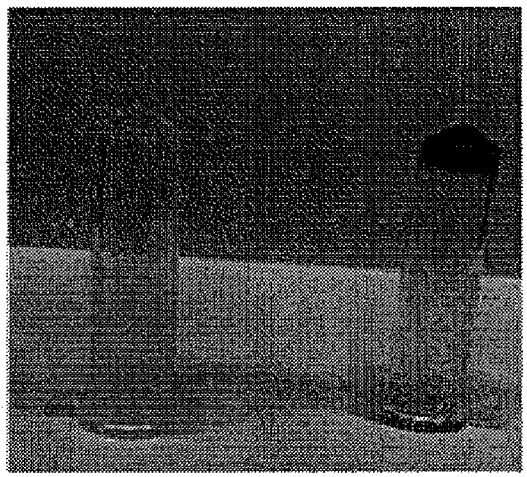
FIG. 11 shows the formation of chitosan hydrogel prepared in Experimental Example 7.

In result, as shown in FIG. 11, in the case of the experimental group without tyrosinase, it existed in liquid state, whereas in the case of the experimental group with tyrosinase added, crosslinking progressed and formation of brown hydrogel was observed.

Experimental Example 8: Preparation of Injectable Hydrogel Crosslinked by Tyrosinase Derived from *Burkholderia* (BT_Ty)

Figure 12:
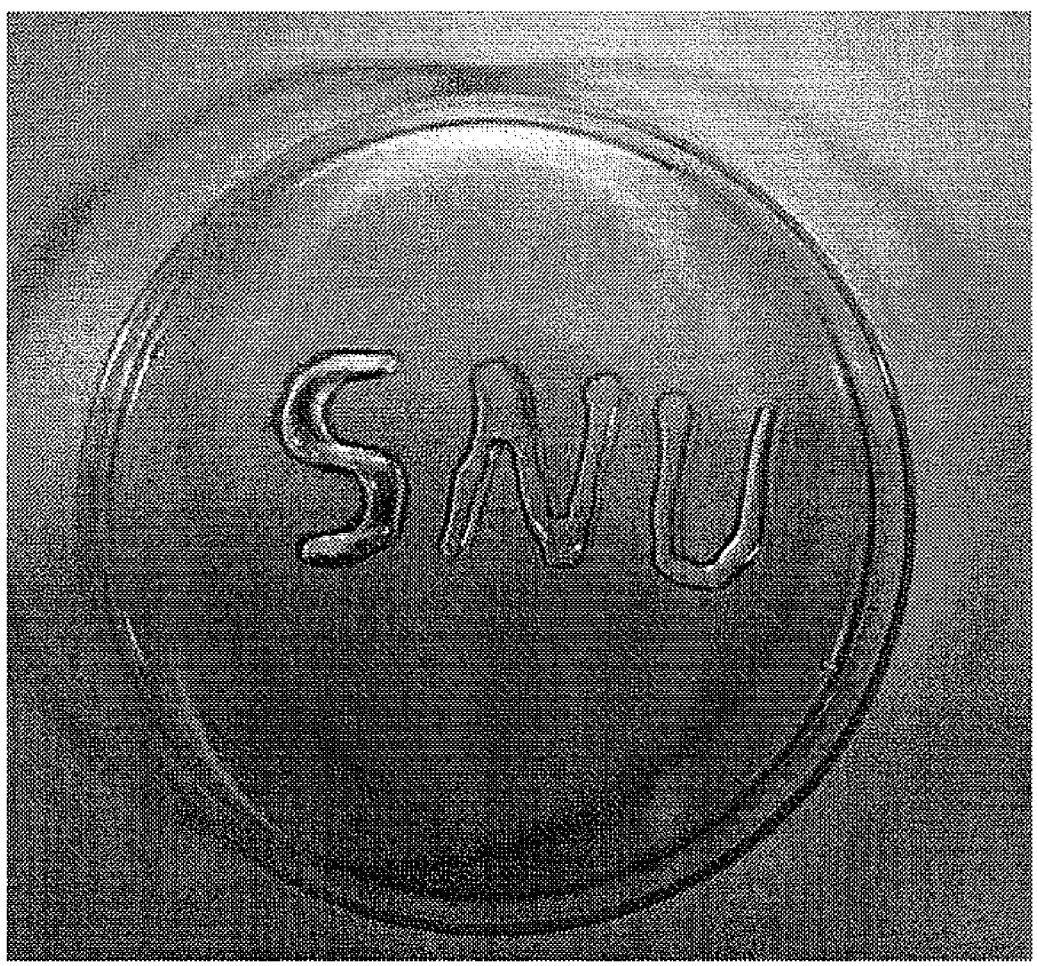
FIG. 12 shows gelatin hydrogel obtained by injecting gelatin hydrogel composition before crosslinking prepared in Experimental Example 8 into a syringe and spraying it in the desired shape (SNU).

10 wt % of gelatin was dissolved in a citric acid buffer solution (pH 4.0), and the temperature was set to 37° C., and 6 μM of tyrosinase was added and mixed, and then the mixed gelatin solution was injected through a syringe, and a desired shape was made. Thereafter, as a result of the crosslinking progressed, as shown in FIG. 12, it was verified that the preparation of hydrogen demonstrating the desired shape (SNU) was possible.

INDUSTRIAL APPLICABILITY

The adhesive hydrogel composition of the present invention is applicable basically in tissue engineering, and furthermore, in pharmaceutical field related to surgery and clinical phases, and in particular, it is applicable in various biopharmaceutical applications such as moisture supply, wound treatment, pollutant blocking, formation of structures such as artificial cartilages, and prevention of adhesion, etc. Moreover, the adhesive hydrogel composition of the present invention is also applicable for use in 3D printing.

What is claimed is:

1. A method for preparing an adhesive hydrogel composition, the method comprising:
cross-linking a polymer or gelatin, using tyrosinase from *Burkholderia*,
wherein the polymer is prepared by introducing tyramine to hyaluronic acid.

2. The method for preparing an adhesive hydrogel composition according to claim 1, wherein the cross-linking is performed in acidic condition.

3. The method for preparing an adhesive hydrogel composition according to claim 1, wherein the tyrosinase is tyrosinase from *Burkholderia thailandensis*.

* * * * *